(12) United States Patent
Hartley et al.

(10) Patent No.: US 7,664,546 B2
(45) Date of Patent: Feb. 16, 2010

(54) POSTURE DETECTION SYSTEM AND METHOD

(75) Inventors: Jesse W. Hartley, Lino Lakes, MN (US); Jeffrey E. Stahmann, Ramsey, MN (US); Kent Lee, Shoreview, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 301 days.

(21) Appl. No.: 10/943,079

(22) Filed: Sep. 15, 2004

(65) Prior Publication Data

US 2005/0145246 A1 Jul. 7, 2005

Related U.S. Application Data

(60) Provisional application No. 60/504,357, filed on Sep. 18, 2003.

(51) Int. Cl.
*A61N 1/365* (2006.01)

(52) U.S. Cl. .......................................................... 607/2

(58) Field of Classification Search ................... 607/3, 607/6, 17–19, 42; 600/529; 128/200.24, 128/206.21, 204.18, 204.21
See application file for complete search history.

(56) References Cited

U.S. PATENT DOCUMENTS

| | | |
|---|---|---|
| 4,365,636 A | 12/1982 | Barker |
| 4,562,841 A | 1/1986 | Brockway et al. |
| 4,702,253 A | 10/1987 | Nappholz et al. |
| 4,827,935 A | 5/1989 | Geddes et al. |
| 5,036,849 A | 8/1991 | Hauck et al. |
| 5,105,354 A | 4/1992 | Nishimura |
| 5,146,918 A | 9/1992 | Kallok et al. |
| 5,158,089 A * | 10/1992 | Swezey et al. .............. 600/595 |
| 5,178,156 A | 1/1993 | Takishima et al. |
| 5,199,424 A | 4/1993 | Sullivan et al. |
| 5,203,348 A | 4/1993 | Dahl et al. |
| 5,230,337 A | 7/1993 | Dahl et al. |

(Continued)

FOREIGN PATENT DOCUMENTS

| | | |
|---|---|---|
| EP | 0 940 155 A | 8/1999 |
| EP | 0940155 | 9/1999 |
| EP | 1151718 | 11/2001 |
| EP | 1317943 | 6/2003 |
| WO | 99/04841 | 2/1999 |

(Continued)

OTHER PUBLICATIONS

Waldemark, Katrina et al., Detection of Apnea Using Short Window FFT Technique and Artificial Neural Network, SPIE, 3390 International Society for Optical Engineering 122-133 (1998).

(Continued)

*Primary Examiner*—Angela D Sykes
*Assistant Examiner*—Amanda Patton
(74) *Attorney, Agent, or Firm*—Hollingsworth & Funk, LLC

(57) ABSTRACT

A posture detection system includes an implantable device and a patient-external respiratory therapy device coupled via a communications channel. At least one of the implantable device and the patient-external respiratory therapy devices includes a posture detector. Posture information is transferred between the implantable device and the patient-external respiratory therapy device. The posture information may be used in connection with sleep detection or to modify therapy delivered by the implantable cardiac device and/or the patient-external respiratory therapy device.

21 Claims, 10 Drawing Sheets

U.S. PATENT DOCUMENTS

| | | | |
|---|---|---|---|
| 5,233,983 A | 8/1993 | Markowitz | |
| 5,245,095 A | 9/1993 | Graves et al. | |
| 5,245,995 A | 9/1993 | Sullivan et al. | |
| 5,284,136 A | 2/1994 | Hauck et al. | |
| 5,313,953 A | 5/1994 | Yomtov et al. | |
| 5,335,657 A | 8/1994 | Terry, Jr. et al. | |
| 5,353,788 A | 10/1994 | Miles | |
| 5,360,442 A | 11/1994 | Dahl et al. | |
| 5,366,496 A | 11/1994 | Dahl et al. | |
| 5,376,476 A | 12/1994 | Eylon | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,411,031 A | 5/1995 | Yomtov | |
| 5,485,851 A | 1/1996 | Erickson | |
| 5,490,502 A * | 2/1996 | Rapoport et al. | 128/204.23 |
| 5,522,382 A | 6/1996 | Sullivan et al. | |
| 5,540,727 A | 7/1996 | Tockman et al. | |
| 5,545,202 A | 8/1996 | Dahl et al. | |
| 5,593,431 A * | 1/1997 | Sheldon | 607/19 |
| 5,603,732 A | 2/1997 | Dahl et al. | |
| 5,738,102 A | 4/1998 | Lemelson | |
| 5,814,087 A | 9/1998 | Renirie | |
| 5,826,579 A | 10/1998 | Remmers et al. | |
| 5,836,987 A | 11/1998 | Baumann et al. | |
| 5,861,011 A | 1/1999 | Stoop | |
| 5,916,243 A | 6/1999 | KenKnight et al. | |
| 5,944,680 A | 8/1999 | Christopherson et al. | |
| 5,974,340 A | 10/1999 | Kadhiresan | |
| 5,974,349 A | 10/1999 | Levine | |
| 6,015,388 A | 1/2000 | Sackner et al. | |
| 6,044,297 A | 3/2000 | Sheldon et al. | |
| 6,044,298 A | 3/2000 | Salo et al. | |
| 6,047,203 A | 4/2000 | Sackner et al. | |
| 6,055,454 A | 4/2000 | Heemels | |
| 6,064,910 A | 5/2000 | Andersson et al. | |
| 6,091,973 A | 7/2000 | Colla et al. | |
| 6,120,441 A | 9/2000 | Griebel | |
| 6,126,611 A | 10/2000 | Bourgeois et al. | |
| 6,128,534 A | 10/2000 | Park et al. | |
| 6,132,384 A | 10/2000 | Christopherson et al. | |
| 6,155,976 A | 12/2000 | Sackner et al. | |
| 6,168,568 B1 | 1/2001 | Gavriely | |
| 6,221,011 B1 | 4/2001 | Bardy | |
| 6,251,126 B1 | 6/2001 | Ottenhoff et al. | |
| 6,261,238 B1 | 7/2001 | Gavriely | |
| 6,269,269 B1 | 7/2001 | Ottenhoff et al. | |
| 6,270,457 B1 | 8/2001 | Bardy | |
| 6,272,377 B1 | 8/2001 | Sweeney et al. | |
| 6,277,072 B1 | 8/2001 | Bardy | |
| 6,280,380 B1 | 8/2001 | Bardy | |
| 6,287,264 B1 | 9/2001 | Hoffman | |
| 6,312,378 B1 | 11/2001 | Bardy | |
| 6,336,903 B1 | 1/2002 | Bardy | |
| 6,357,444 B1 | 3/2002 | Parker | |
| 6,358,203 B2 | 3/2002 | Bardy | |
| 6,363,270 B1 | 3/2002 | Colla et al. | |
| 6,368,284 B1 | 4/2002 | Bardy | |
| 6,368,287 B1 | 4/2002 | Hadas | |
| 6,398,727 B1 * | 6/2002 | Bui et al. | 600/300 |
| 6,398,728 B1 | 6/2002 | Bardy | |
| 6,398,739 B1 | 6/2002 | Sullivan et al. | |
| 6,409,675 B1 | 6/2002 | Turcott | |
| 6,415,183 B1 | 7/2002 | Scheiner et al. | |
| 6,438,407 B1 | 8/2002 | Ousdigian et al. | |
| 6,440,066 B1 | 8/2002 | Bardy | |
| 6,480,733 B1 | 11/2002 | Turcott | |
| 6,514,218 B2 * | 2/2003 | Yamamoto | 600/587 |
| 6,527,729 B1 | 3/2003 | Turcott | |
| 6,574,507 B1 | 6/2003 | Bonnet | |
| 6,580,944 B1 | 6/2003 | Katz et al. | |
| 6,589,188 B1 | 7/2003 | Street et al. | |
| 6,600,949 B1 | 7/2003 | Turcott | |
| 6,606,993 B1 | 8/2003 | Wiesmann et al. | |
| 6,641,542 B2 | 11/2003 | Cho et al. | |
| 6,658,292 B2 | 12/2003 | Kroll et al. | |
| 6,741,885 B1 | 5/2004 | Park et al. | |
| 6,752,765 B1 * | 6/2004 | Jensen et al. | 600/536 |
| 6,752,766 B2 | 6/2004 | Kowallik et al. | |
| 6,810,287 B2 | 10/2004 | Zhu et al. | |
| 6,857,428 B2 * | 2/2005 | Thornton | 128/206.21 |
| 6,881,192 B1 | 4/2005 | Park | |
| 6,964,641 B2 | 11/2005 | Cho et al. | |
| 7,025,730 B2 * | 4/2006 | Cho et al. | 600/529 |
| 7,189,204 B2 | 3/2007 | Ni et al. | |
| 7,225,013 B2 | 5/2007 | Geva et al. | |
| 7,400,928 B2 | 7/2008 | Hatlestad et al. | |
| 2001/0031930 A1 | 10/2001 | Roizen et al. | |
| 2002/0193697 A1 | 12/2002 | Cho et al. | |
| 2002/0193839 A1 | 12/2002 | Cho et al. | |
| 2003/0023184 A1 | 1/2003 | Pitts-Crick et al. | |
| 2003/0100925 A1 | 5/2003 | Pape et al. | |
| 2003/0153953 A1 | 8/2003 | Park et al. | |
| 2003/0153954 A1 | 8/2003 | Park et al. | |
| 2003/0153955 A1 | 8/2003 | Park et al. | |
| 2003/0153956 A1 | 8/2003 | Park et al. | |
| 2003/0187336 A1 | 10/2003 | Odagiri et al. | |
| 2003/0195571 A1 | 10/2003 | Burnes et al. | |
| 2003/0199945 A1 | 10/2003 | Ciulla | |
| 2003/0204213 A1 | 10/2003 | Jensen et al. | |
| 2004/0002742 A1 | 1/2004 | Florio | |
| 2004/0030362 A1 | 2/2004 | Hill et al. | |
| 2004/0088027 A1 | 5/2004 | Burnes et al. | |
| 2004/0116981 A1 | 6/2004 | Mazar | |
| 2004/0122488 A1 | 6/2004 | Mazar et al. | |
| 2004/0128161 A1 | 7/2004 | Mazar et al. | |
| 2004/0133079 A1 | 7/2004 | Mazar et al. | |
| 2004/0138719 A1 | 7/2004 | Cho et al. | |
| 2004/0163648 A1 * | 8/2004 | Burton | 128/204.21 |
| 2004/0210155 A1 | 10/2004 | Takemura et al. | |
| 2005/0039745 A1 | 2/2005 | Stahmann et al. | |
| 2005/0043652 A1 | 2/2005 | Lovett et al. | |
| 2005/0043772 A1 | 2/2005 | Stahmann et al. | |
| 2007/0161873 A1 | 7/2007 | Ni et al. | |
| 2007/0282215 A1 | 12/2007 | Ni et al. | |

FOREIGN PATENT DOCUMENTS

| | | |
|---|---|---|
| WO | WO0001438 | 1/2000 |
| WO | WO 00/17615 | 3/2000 |
| WO | 02/087696 | 11/2002 |
| WO | WO2004062485 | 7/2004 |
| WO | WO2005028029 | 3/2005 |

OTHER PUBLICATIONS

Altshule et al., The Effect of Position on Periodic Breathing in Chronic Cardiac Decomposition, New Eng. Journal of Med., vol. 259, No. 22, pp. 1064-1066, Nov. 27, 1958.

Dark et al., Breathing Pattern Abnormalities and Arterial Oxygen Desaturation During Sleep in the Congestive Heart Failure Syndrome, Chest, Jun. 1987, 6:833-6.

Hoffman et al., Cheyne-Stokes Respiration in Patients Recovering from Acute Cardiogenic Pulmonary Edema, Chest 1990, 97:410-12. Abstract Only.

Junyu et al., Posture Detection Algorithm Using Multi Axis DC-Accelerometer, Pace vol. 22, Apr. 1999.

Rees et al., Paroxysmal Nocturnal Dyspnoea and Periodic Respiration, The Lancet, Dec. 22-29, 1979, pp. 1315-1317. Abstract Only.

Tkacova et al., Left Ventricular Volume in Patients with Heart Failure and Cheyne-Strokes Respiration during Sleep, Am. Journal, Respir. Crit. Care Med., vol. 156, pp. 1549-1555, 1997.

* cited by examiner

POSTURE DETECTION SYSTEM AND METHOD

RELATED PATENT DOCUMENT

This application claims the benefit of Provisional Patent Application Ser. No. 60/504,357, filed on Sep. 18, 2003, to which priority is claimed pursuant to 35 U.S.C. §119(e) and which is hereby incorporated herein by reference.

FIELD OF THE INVENTION

The present invention relates generally to methods and systems for detecting patient posture.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiration system, through the breathing mechanism, performs the function of exchanging these gases with the external environment. Together, the cardiac and respiration systems form a larger anatomical and functional unit denoted the cardiopulmonary system.

Various disorders may affect the cardiovascular, respiratory, and other physiological systems. For example, heart failure is a clinical syndrome that impacts a number of physiological processes. Heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion.

Implantable cardiac rhythm management systems have been used as an effective treatment for patients with serious cardiac arrhythmias such as those associated with CHF. Implantable cardiac rhythm management devices may include implanted pacemakers, implanted defibrillators, implanted ventricular synchronization devices or devices that combination two or more of these functions. These systems typically include one or more leads and circuitry to sense signals from the interior and/or exterior surfaces of the heart. Such systems also include circuitry for generating electrical pulses which are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating various arrhythmias.

Disordered breathing is a respiratory disorder that has been linked to congestive heart failure. Disordered breathing, including apnea and hypopnea, may be caused, for example, by an obstructed airway, or by derangement of the signals from the brain controlling respiration. Sleep disordered breathing is particularly prevalent and is associated with excessive daytime sleepiness, systemic hypertension, increased risk of stroke, angina, and myocardial infarction.

Disordered breathing can be particularly serious for patients concurrently suffering from cardiovascular deficiencies, such as those associated with CHF.

Disordered breathing is often treated by an airway pressure device. Such a device applies a positive air pressure to the patient through a respiration mask. The application of the positive air pressure serves to keep the patient's airway open, allowing the patient to breath normally.

Because of the complex interactions between the cardiovascular, pulmonary and other systems, a coordinated approach to monitoring, diagnosis, and treatment of various disorders is needed.

SUMMARY OF THE INVENTION

Embodiments of the invention relate to detection of patient posture. One embodiment of the invention involves a posture detection system including an implantable cardiac device and a patient-external respiratory therapy device. The implantable cardiac device and the patient-external respiratory therapy device are coupled by a communications channel configured to transfer at least posture information between the implantable cardiac device and a patient-external respiratory therapy device.

According to one aspect of the invention, the patient-external respiratory therapy device includes components of the posture detector. For example, the posture detector may be positioned on the respiratory mask or the respiratory mask strap. In another example, the posture detector may be positioned on the patient's body and communicatively coupled to a control unit of the respiratory therapy device through a lead. The patient-external respiratory therapy device transmits posture information to the implantable cardiac device.

According to another aspect of the invention, the implantable cardiac device includes components of the posture detector. The implantable cardiac device transmits posture information to the patient-external respiratory therapy device.

Another embodiment of the invention involves a posture detection method. The posture detection method includes detecting posture using a sensor of a patient-external respiratory therapy device or a sensor of an implantable cardiac device. The posture information is transmitted between the patient-external respiratory therapy device and the implantable cardiac device.

According to various aspects of the invention, the posture information may be used to adjust therapy delivered to the patient. The therapy adjusted may include a therapy delivered by the implantable device, or by the external respiratory therapy device. In one implementation, the implantable device delivers a cardiac electrical stimulation therapy and the cardiac electrical stimulation therapy is adjusted based on patient posture. Alternatively, or additionally, therapy delivered by the respiratory therapy device may be modified using the posture information.

The above summary of the invention is not intended to describe each embodiment or every implementation of the invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIG. 4 illustrates a block diagram of a medical system in accordance with embodiments of the invention which includes respiratory therapy device communicatively coupled to a CRM system;

Figure 1:
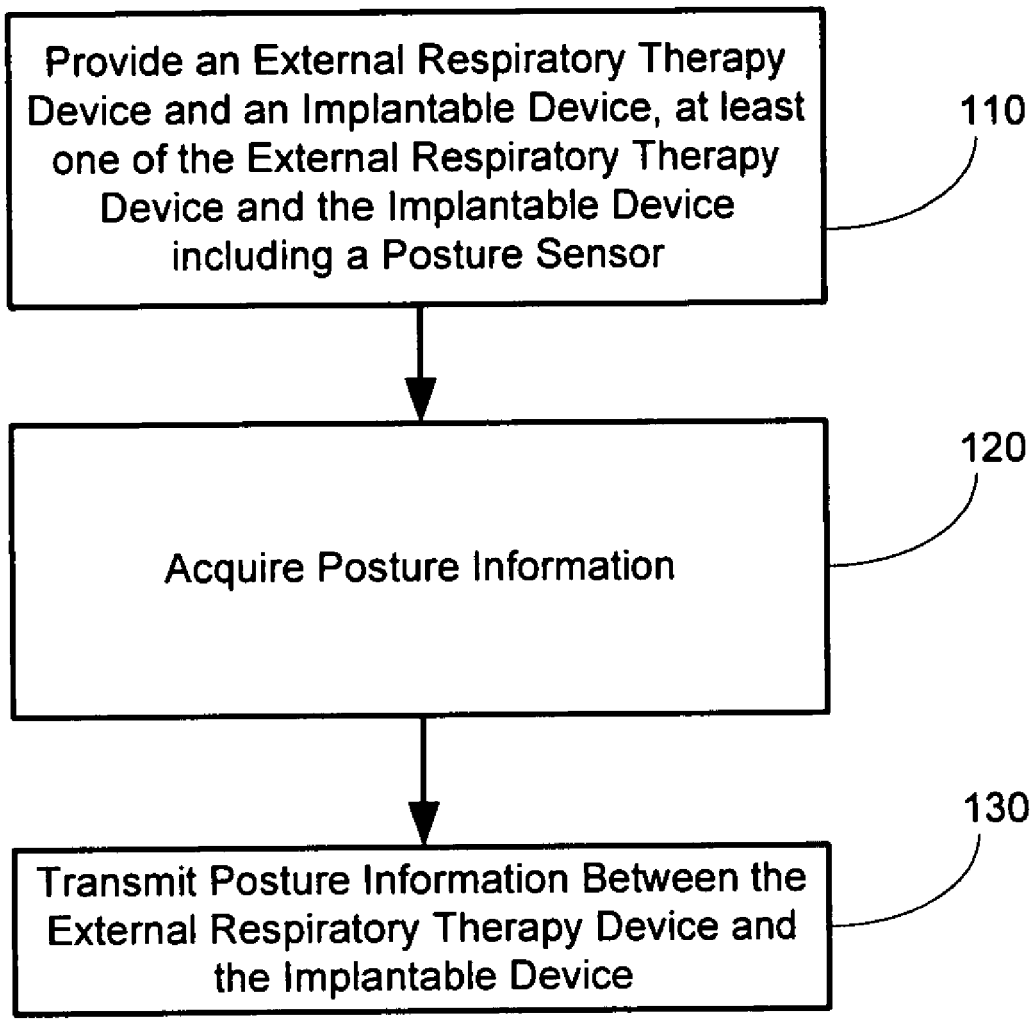
FIG. 1 is a flow chart of a method for posture detection in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

The present invention relates to detecting patient posture using a posture sensor disposed on an external respiratory therapy device. Posture information is transmitted to an implantable device, such as an implantable pacemaker, defibrillator, or implantable device. Posture detection may involve, for example, determining a positional orientation of the patient's body or the positional orientation of a portion of the patient's body, such as the patient's torso. Posture detection includes discriminating between a horizontal, recumbent or supine position and a vertical or upright position, determining an inclination of a portion of the patient's body, and or determining if the patient is lying on his or her side, back, or front. Knowledge of patient posture may be used by the implantable device to diagnose various patient disorders and/or to adjust patient therapy, for example. A supine posture is more likely to result in obstruction of the upper airway and can be used to predict episodes of obstructive hypopnea and apnea, for example.

Discriminating between a recumbent and an upright position of the patient's body is useful in connection with determining if a patient is asleep or awake. Patient posture can be used as an indicator or verifier that a patient is sleeping. Diagnosis of various conditions, e.g., sleep apnea, may be enhanced with knowledge of the patient's sleep state. Thus, a patient may be diagnosed as having sleep disordered breathing if breathing interruptions occur while a patient is sleeping, as indicated by patient posture during the disordered breathing episodes.

The position of the patient's body, such as the inclination of the upper torso, may predispose the patient to various medical disorders, including disorders affecting the respiratory, cardiopulmonary, and/or cardiovascular systems. Information about patient position may be evaluated with respect to the detection of various disorders to determine if an association between patient position and a particular disorder is present.

Knowledge of patient posture may enhance therapy delivery. Therapy may be adjusted to provide a more appropriate therapy based on whether the patient is asleep or awake. For example, a cardiac pacing rate may be decreased from a waking rate to a lower sleeping rate to account for the decreased hemodynamic need of the patient during sleep.

Some patients suffer from a number of disorders that are treated with multiple therapy devices. For example, a patient suffering from cardiac and respiratory problems may receive therapy from an implantable cardiac rhythm management system, e.g., a bi-ventricular pacing device for synchronizing ventricular contractions, and an external respiratory therapy device. Using therapy devices in a coordinated manner provides opportunities for enhanced monitoring, diagnosis and/or therapy delivery. Various embodiments described herein are directed to a posture sensor disposed on a respiratory therapy mask. Information related to patient posture is transmitted to an implantable device, such as a cardiac therapy device.

FIG. 1 is a flowchart of a method for determining patient posture. At least one of a patient-external respiratory device and an implantable device include 110 a posture detector. The posture detector, which may be positioned on a component of the respiratory therapy device, within an implantable housing of the implantable device, or in other locations, acquires 120 patient posture information. The posture information is transmitted 130 to between the patient-external respiratory device and the implantable device.

In a one configuration, the posture detector is coupled by a wire lead to the controller unit of the respiratory therapy device. Communications circuitry positioned within the controller unit wirelessly transmits the posture information, possibly along with other relevant information, to the implantable device. In another configuration, the circuitry for wirelessly transmitting the posture information to the implantable device is disposed with the posture sensor on the respiratory mask or mask strap, for example.

In another configuration, the posture detector is disposed within a housing of an implantable device. Communications circuitry positioned within the implantable device housing wirelessly transmits the posture information to the control unit of the respiratory therapy device, possibly along with other relevant information.

In yet another configuration, the posture information may be relayed from one device to another device through a patient information server, such as is used in an advanced patient management system.

Figure 2:
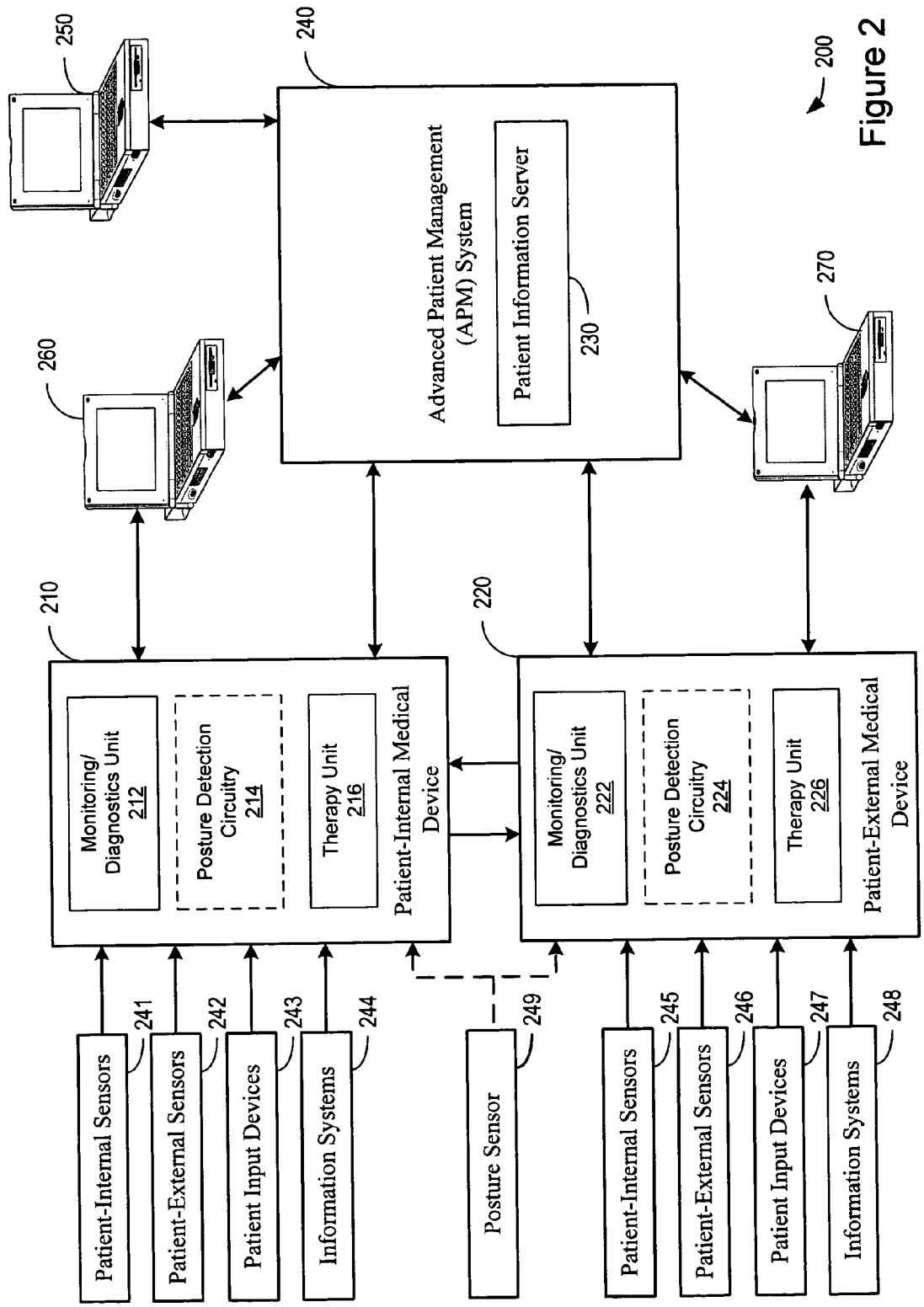
FIG. 2 is a block diagram of a medical system that may be used to implement coordinated patient measuring and/or monitoring, diagnosis, and/or therapy, including detecting patient posture in accordance with embodiments of the invention.

FIG. 2 is a block diagram of a medical system 200 that may be used to implement coordinated patient monitoring, diagnosis, and/or therapy, including patient posture detection in accordance with embodiments of the invention. The medical system 200 includes an implantable medical device 210, such as an implantable cardiac rhythm management (CRM) system, pacemaker, defibrillator, cardiac resynchronizer or cardiac monitor, for example. The system includes a patient-external respiratory therapy device 220. Each of the patient-internal 210 and patient-external 220 medical devices may include a patient monitoring and diagnostics unit 212, 222, and/or a therapy unit 216, 226.

The patient-internal medical device 210 is typically a fully or partially implantable device that performs measuring, monitoring, diagnosis, and/or therapy functions. The patient-external respiratory therapy device 220 may perform monitoring, diagnosis, and/or therapy functions external to the patient (i.e., not invasively implanted within the patient's body). The patient-external respiratory therapy device 220 typically includes controller unit that controls pressure delivered to the patient's airway through tubing and a respiratory facial or nasal mask. The respiratory mask may be held in place using a strap or other device.

The patient-internal device 210 and the patient-external respiratory therapy device 220 may be coupled to one or more sensors 241, 242, 245, 246, patient input devices 243, 247, and/or other information acquisition devices 244, 248. The sensors 241, 242, 245, 246, patient input devices 243, 247, and/or other information acquisition devices 244, 248 may be employed to detect conditions relevant to the monitoring, diagnostic, and/or therapeutic functions of the patient-internal and patient-external medical devices 210, 220.

The medical devices 210, 220 may each be coupled to one or more patient-internal sensors 241 that are fully or partially implantable within the patient. The medical devices 210, 220 may be coupled to patient-external sensors 242 positioned on, near, or in a remote location with respect to the patient. The patient-internal and patient-external sensors are used to sense conditions, such as physiological or environmental conditions, that affect the patient.

The medical devices 210, 220 may be coupled to one or more patient input devices 243, 247. The patient input devices are used to allow the patient to manually transfer information to the medical devices 210, 220. The patient input devices 243, 247 may be particularly useful for inputting information concerning patient perceptions, such as how well the patient feels, and information such as patient bed time and wake-up time, drug use, or other activities that are not automatically sensed or detected by the medical devices 210, 220.

The medical devices 210, 220 may be connected to one or more information acquisition devices 244, 248, for example, a database that stores information useful in connection with the monitoring, diagnostic, or therapy functions of the medical devices 210, 220. For example, one or more of the medical devices 210, 220 may be coupled through a network to a patient information server 230 that provides information about environmental conditions affecting the patient, e.g., the pollution index for the patient's location.

The patient-internal sensors 241 may be coupled to the patient-internal medical device 210 through one or more internal leads. In one example, an internal endocardial lead system is used to couple cardiac electrodes to an implantable pacemaker or other cardiac rhythm management device. One or more of the patient-internal sensors 241 may be equipped with transceiver circuitry to support wireless communications between the one or more patient-internal sensors 241 and the patient-internal medical device 210. The patient-external sensors 242, patient input device 243, and information systems 244 may be coupled to the patient-internal medical device 210 through wireless connections.

The patient-internal sensors 245 may be coupled to the patient-external respiratory device 220 through a wireless communications link. Patient-external sensors 246, patient input device 247, and information systems 248 may be coupled to the external respiratory therapy device 220 through wired leads or wireless connections.

A posture sensor 249 may be communicatively coupled to the circuitry of the patient-internal medical device 210 and/or the circuitry of the external respiratory therapy device 220 through leads or through a wireless connection. The posture sensor 249 generates a signal modulated by patient posture.

Figure 3:
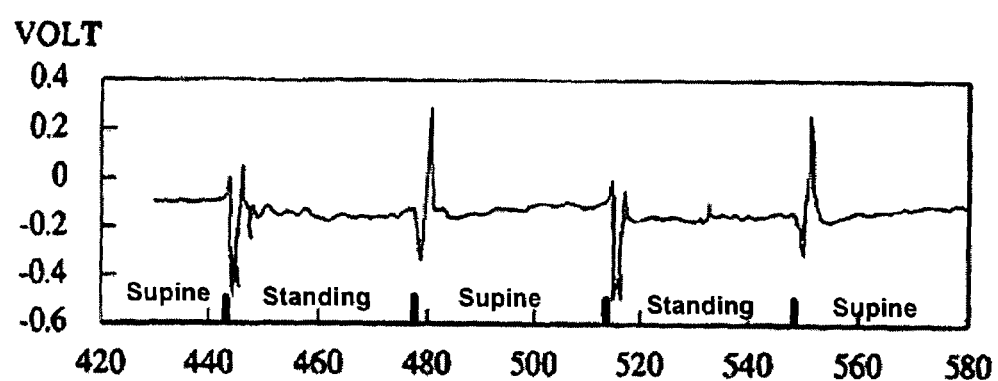
FIG. 3 is a graph representative of accelerometer signals associated with a patient moving from a standing to supine or supine to standing position.

Posture sensing may employ various types of sensors, including, for example, multiaxis accelerometers, inclination sensors, magnetometers, mercury-type switches, or other sensing methodologies. In one implementation, an accelerometer is used as a posture sensor. FIG. 3 is a waveform signal generated by an accelerometer that indicates patient posture. When a patient moves from a supine position to an upright position, the accelerometer produces fluctuating waveform signals. When a patient is supine and moves to an upright standing position, a negative change in voltage on the waveform occurs, e.g. from 0 Volts to −0.5 Volts. When a patient is in the standing position and moves to a supine position, a positive change in voltage on the waveform occurs, e.g. from 0 Volts to 0.25 Volts.

Referring back to FIG. 2, the change in the signal generated by the posture sensor may be detected using detector circuitry 214, 224 positioned near the posture sensor, e.g., on the respiratory mask or respiratory mask strap. In other configurations posture detection circuitry 224, 214 may be disposed within the housing of the external respiratory therapy device housing and/or within the housing of the implantable device.

In one embodiment, the patient-internal medical device 210 and the patient-external medical device 220 may communicate through a wireless link between the medical devices 210, 220. For example, the patient-internal and patient-external devices 210, 220 may be coupled through a short-range radio link, such as Bluetooth, IEEE 802.11, and/or a proprietary wireless protocol. Such a communications link may facilitate uni-directional or bi-directional communication between the patient-internal device 210, external respiratory therapy device 220, and or external processing systems 230, device programmers or terminals 260, 270, 250, sensors 241, 242, 245, 246, 249, patient input devices 23, 247, and/or information systems 244, 248. In various configurations, posture information, and/or other information may be transmitted between the patient-internal device 210 and the external respiration therapy device 220 to enhance and/or coordinate the functions of the medical devices 210, 220.

In one configuration, the patient-internal and patient-external medical devices 210, 220 may be used within the structure of an advanced patient management system 240. Advanced patient management systems 240 involve a system of medical devices that are accessible through various communications technologies. For example, patient data, including posture information, may be downloaded from one or more of the medical devices periodically or on command, and stored at the patient information server 230. The physician and/or the patient may communicate with the medical devices and the patient information server 230, for example, to acquire patient data or to initiate, terminate or modify therapy.

The data stored on the patient information server 230 may be accessible by the patient and the patient's physician through one or more terminals 250, e.g., remote computers located in the patient's home or the physician's office. The patient information server 230 may be used to communicate with one or more of the patient-internal and patient-external medical devices 210, 220 to provide remote control of the monitoring, diagnosis, and/or therapy functions of the medical devices 210, 220.

In one embodiment, the patient's physician may access patient data transmitted from the medical devices 210, 220 to the patient information server 230. After evaluation of the patient data, the patient's physician may communicate with one or more of the patient-internal or patient-external devices 210, 220 through the APM system 240 to initiate, terminate, or modify the monitoring, diagnostic, and/or therapy functions of the patient-internal and/or patient-external medical systems 210, 220. Systems and methods involving advanced patient management techniques are further described in U.S. Pat. Nos. 6,336,903, 6,312,378, 6,270,457, and 6,398,728, hereby incorporated herein by reference.

Various embodiments described herein may be used in connection with advanced patient management. Methods, structures, and/or techniques described herein relating to advanced patient management, such as those involving remote patient/device monitoring, diagnosis, therapy, or other advanced patient management related methodologies, may incorporate features of one or more of the following references: U.S. Pat. Nos. 6,221,011; 6,277,072; 6,280,380; 6,358,203; 6,368,284; and 6,440,066 each hereby incorporated herein by reference.

FIGS. 4A-4D are diagrams illustrating medical systems 400 with posture detection functionality in accordance with embodiments of the invention. The medical system 400 includes a respiratory therapy device 410 communicatively coupled to a CRM system 450. Delivery of cardiac electrical stimulation therapy provided by the CRM system 450, e.g., bradycardia pacing, tachycardia pacing, cardiac resynchronization pacing and/or cardioversion/defibrillation, is controlled by a cardiac therapy control unit 455 disposed within the housing of the CRM system.

The respiratory therapy device 410 may comprise for example, a positive airway pressure (CPAP) device, a nebulizer, ventilator, or other type of respiration therapy device. For the purposes of describing FIGS. 4A-4D, the respiratory therapy device 410 is considered to be a CPAP device. The CPAP device includes a respiratory therapy control unit 411, respiratory mask 420, and tubing 415 coupling the respiratory mask 420 to the control unit 411. Respiratory therapy pressure is controlled by circuitry 426 within the control unit 411. The respiratory therapy control unit 411 develops an airway pressure delivered to the patient through the respiratory mask 420 via tubing 415. Various methodologies and systems for implementing CPAP therapies are described in U.S. Pat. Nos. 5,245,995 and 5,199,424, which are incorporated herein by reference.

The respiratory mask 420 is held in place over the patient's nose and/or mouth using a strap 421 or other type of securing structure. In one embodiment, illustrated in FIG. 4A, a posture detector 425 is positioned on a component of the CPAP device, preferably on the mask 420 or mask strap 421. With the posture detector 425 positioned on the mask 420 or mask strap 421, the sensor produces signals modulated by changes in the position of the patient's torso and/or head. The posture detector 425 is coupled to the respiratory therapy control unit 410 through a lead extending from the mask assembly 420, 421.

Figure 4A:
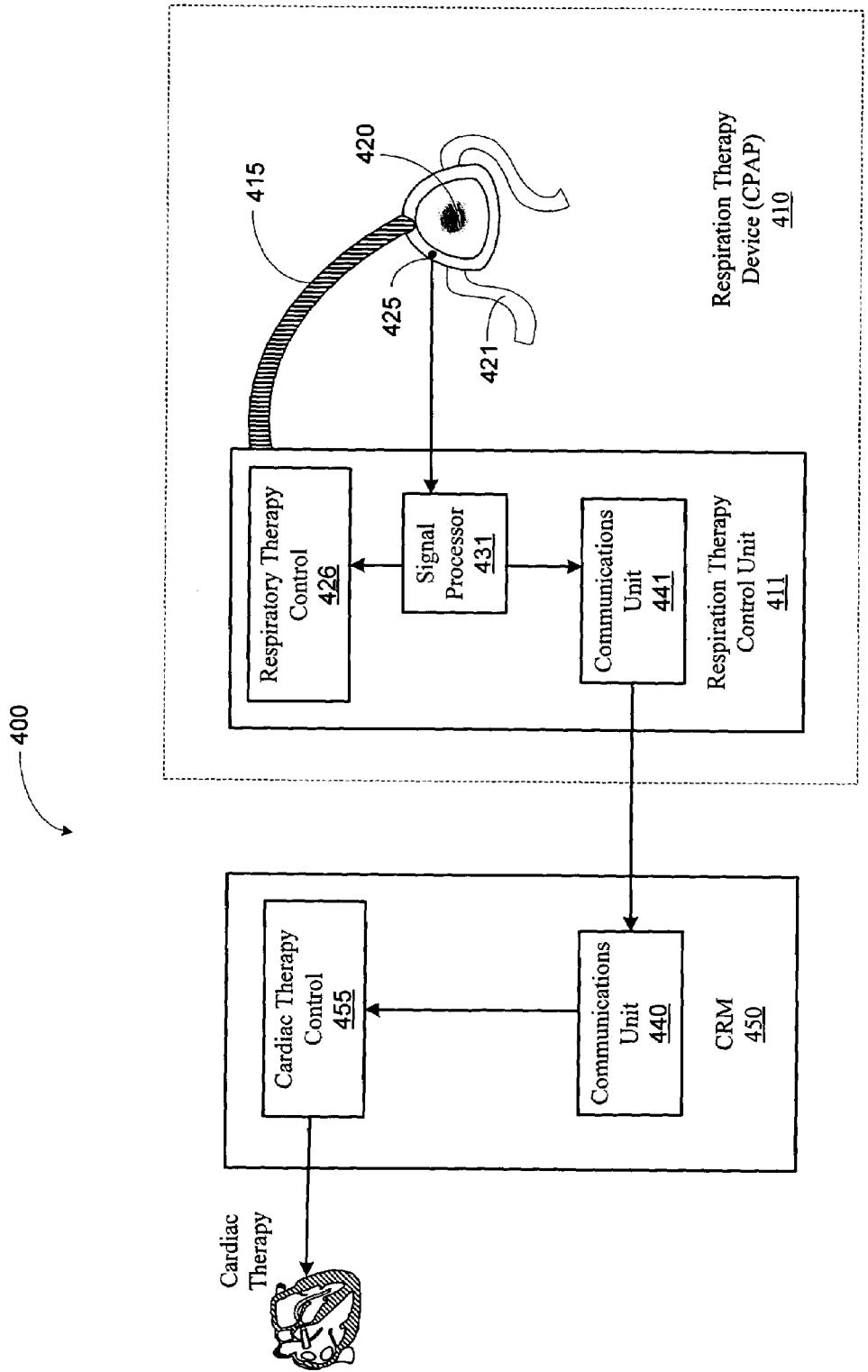
FIGS. 4A-4D are block diagrams illustrating medical systems with posture detection functionality in accordance with embodiments of the invention.
Figure 4B:
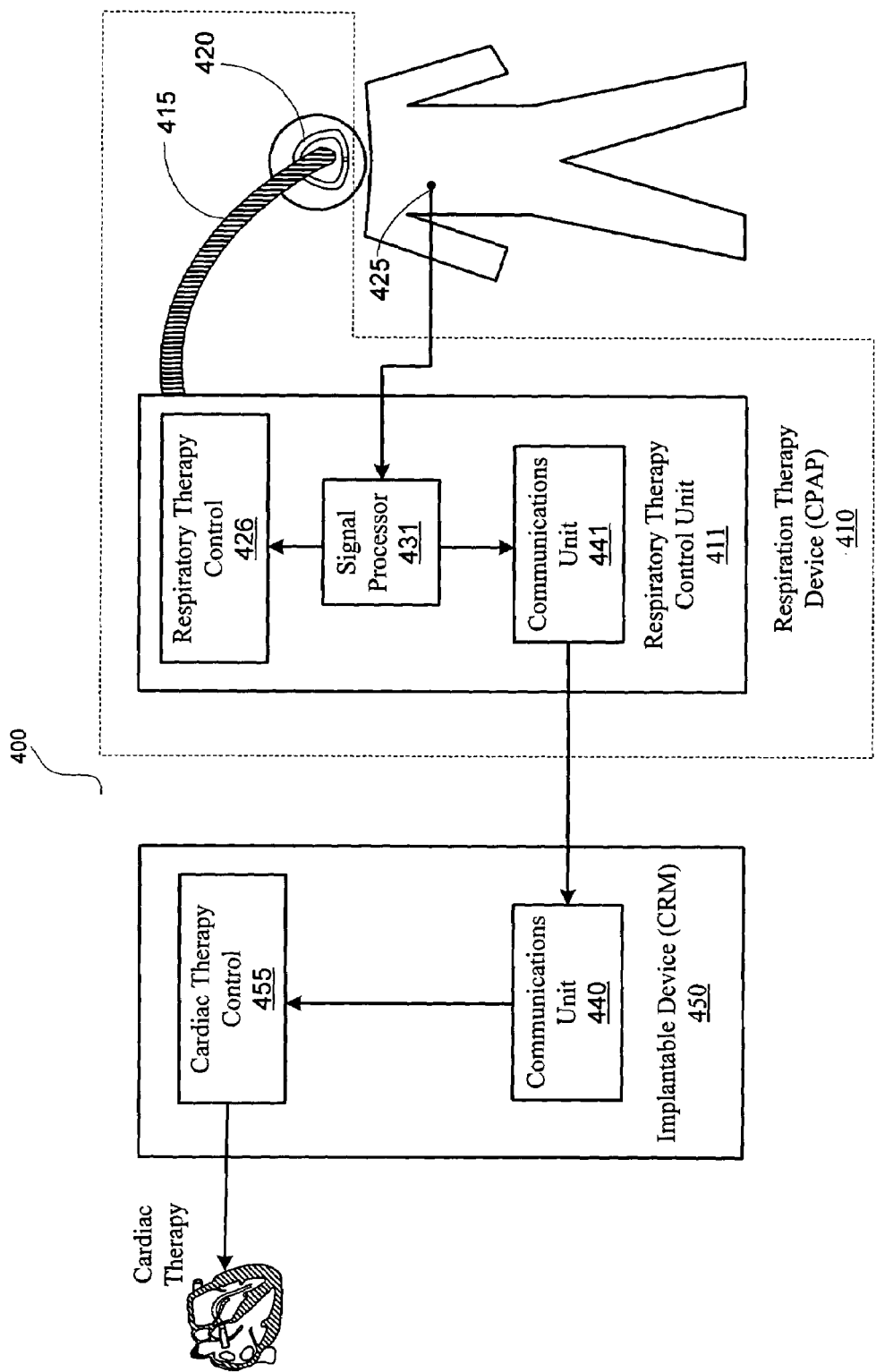

In another embodiment, illustrated in FIG. 4B, one or more posture detectors 425 are positioned on or near the patient so that changes in the patient's posture are detectable by an accelerometer or other sensor used for sensing patient position. The posture detectors 425 may be positioned on or near the patient's head, chest, abdomen, or other appropriate location of the patient's body. The posture detector 425 may be communicatively coupled to the respiratory therapy unit 410 through a wire lead or through a wireless communications link.

The respiratory therapy unit includes a signal processor 431 for energizing the posture detector 425 and/or receiving the signals from the posture detector 425. Compatible communications units 441, 440 of the CPAP 410 and CRM 450 devices establish a wireless communication channel between the CPAP device 410 and the CRM device 450. Posture information is transmitted over the wireless communications channel 440, 441 from the CPAP device 410 to the CRM device 450.

Figure 4C:
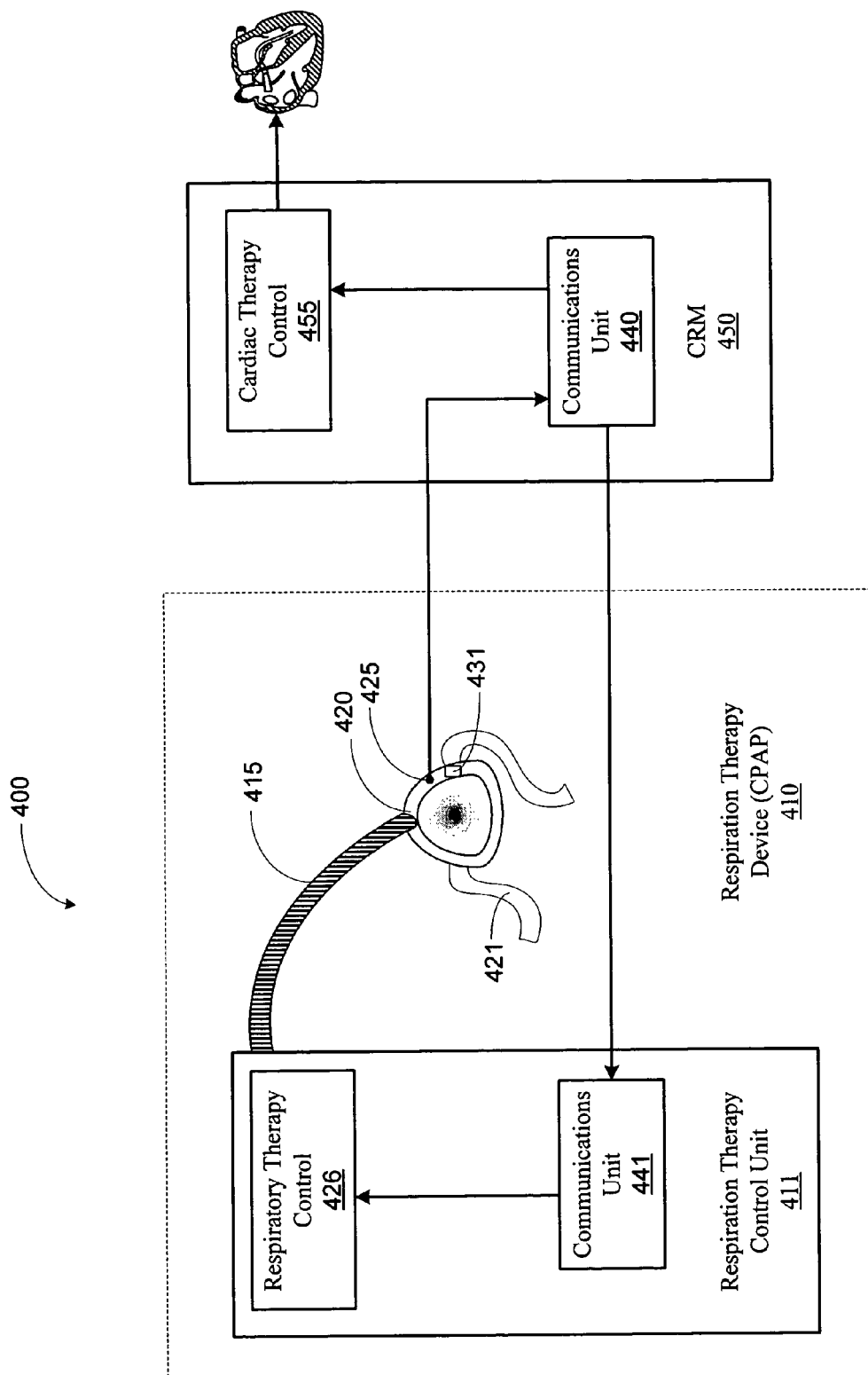

In a further embodiment, illustrated in FIG. 4C, a signal processing circuitry 431, including circuitry for wireless communication is positioned along with the posture detector 425 on the respiratory mask 420 or mask strap 421. In one configuration, the posture detector and processing circuitry 425, 431 are configured to detect patient posture and wirelessly communicate posture information to the implantable device 450. Posture information may also be transferred between the implantable device 450 and the respiratory therapy device 410. In another configuration (not shown), the posture detector and associated circuitry 425, 431 detect patient posture and wirelessly communicate the posture information to the respiratory therapy device 410.

Figure 4D:
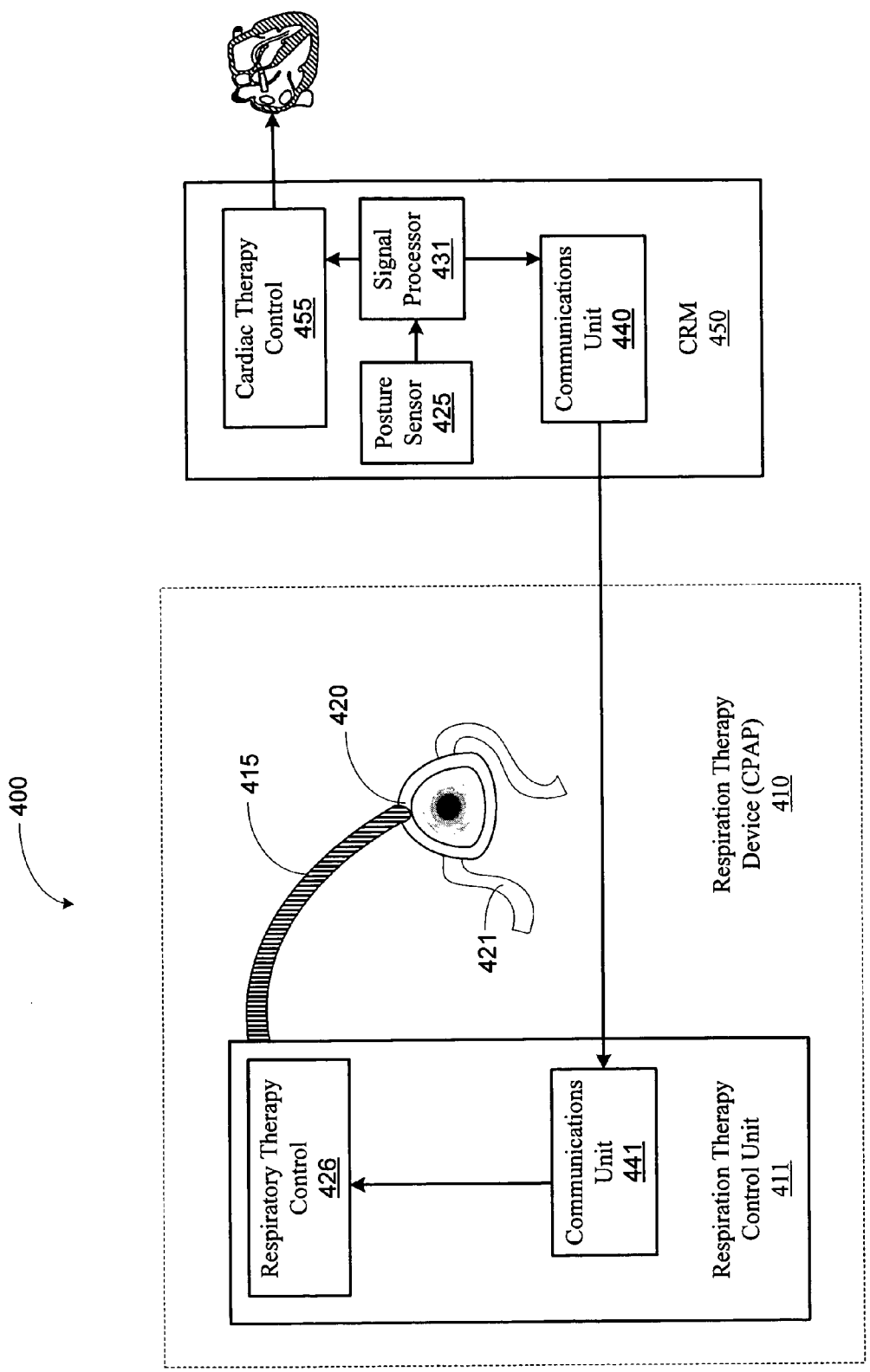

FIG. 4D illustrates another embodiment of a posture detection system. In this embodiment, the implantable device 450 includes the posture sensor 425 and associated circuitry 431. The posture detector 425 may comprise, for example, an accelerometer or other sensor disposed within or on an implantable housing or other component of the implantable device 450. The posture information may be transmitted form the implantable device 450 to the external respiratory therapy device 410.

The CRM device 450 may utilize the received posture information for diagnostic or therapeutic purposes. For example, as previously discussed, the CRM device 450 may use the posture information to detect or confirm sleep. Various methods and systems involving the use of posture information for detection and/or verification of sleep are described in commonly owned U.S. patent application Ser. No. 10/309, 771, filed on Dec. 4, 2002, now U.S. Pat., No. 7,189,204 which is incorporated herein by reference.

The posture information may also be used in connection with detecting or predicting disordered breathing. Further posture information may be used by the CPAP device 410 or the CRM device 450 to correlate patient posture, e.g., particular patient positions or torso inclinations, to episodes of disordered breathing. Methods of detecting disordered breathing using a CPAP device are described in previously incorporated U.S. Pat. Nos. 5,245,995 and 5,199,424. Methods of detecting or predicting disordered breathing based on respiratory patterns and other factors are described in commonly owned U.S. patent application Ser. No. 10/309, 770, filed Dec. 4, 2002, now U.S. Pat. No. 7,252,640 and Ser. No. 10/643,016, filed Aug. 18, 2003, now U.S. Pat. No. 7,396, 333. Correlation of patient posture to detected disordered breathing episodes may be used to enhance detection or prediction of subsequent episodes of disordered breathing.

Posture information may be used by the implantable cardiac device 450 to initiate, modify or terminate a therapy delivered by the CRM device to the patient. For example, based on the posture information, the CRM device may decrease or increase a pacing rate, switch from a uni-ventricular pacing mode to a bi-ventricular pacing mode or the reverse, initiate, modify or terminate cardiac electrical stimulation therapy for disordered breathing. The CPAP device 410 may also utilize the received posture information to adjust the external respiratory therapy delivered by the CPAP device 410. Methods and systems for delivering and adapting cardiac stimulation therapy for disordered breathing, which may be enhanced using posture detection in accordance with the present invention, are described in commonly owned U.S. patent application Ser. Nos. 10/643,203 and 10/643,154, both filed on Aug. 18, 2003, now U.S. Publication Nos. 2005/0039745 and 2005/0043772, and both incorporated herein by reference.

Figure 5A:
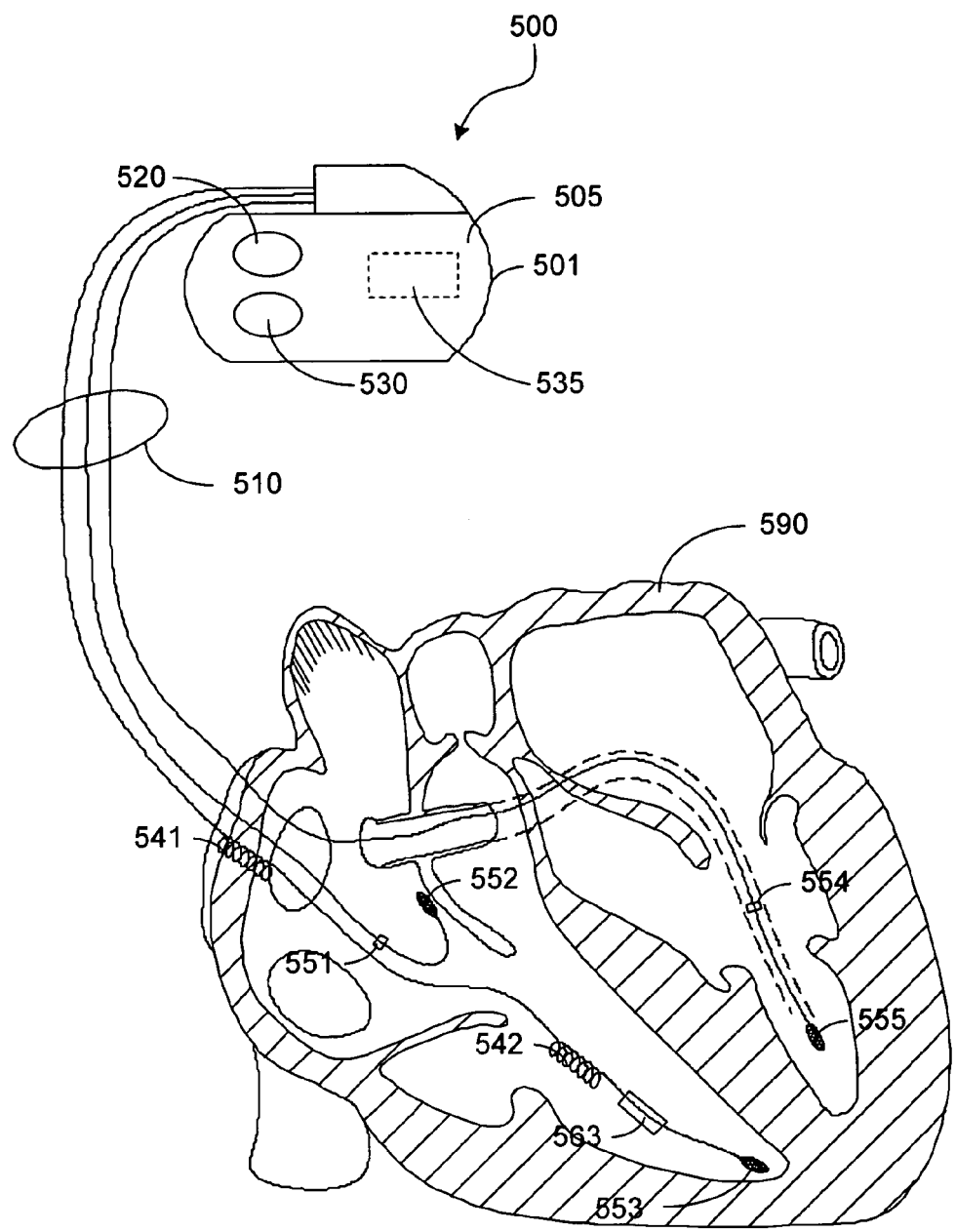
FIG. 5A is a partial view of an implantable device that may include circuitry for implementing portions of the posture detection system in accordance with embodiments of the invention.

FIG. 5A is a partial view of an implantable device that may include circuitry 535 for implementing portions of the posture detection system in accordance with embodiments of the invention. In this example, the implantable device comprises a cardiac rhythm management device (CRM) 500 including an implantable pulse generator 505 electrically and physically coupled to an intracardiac lead system 510. The posture detection system may alternatively be implemented in a variety of implantable monitoring, diagnostic, and/or therapeutic devices, such as an implantable cardiac monitoring device, an implantable drug delivery device, or an implantable neurostimulation device, for example.

Portions of the intracardiac lead system 510 are inserted into the patient's heart 590. The intracardiac lead system 510 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 501 of the pulse generator 505 may optionally serve as a can electrode.

Communications circuitry is disposed within the housing 501 for facilitating communication between the pulse generator 505 and an external communication device, such as a portable or bed-side communication station, patient-carried/worn communication station, or external programmer, for example. The communications circuitry can also facilitate unidirectional or bidirectional communication with one or more implanted, external, cutaneous, or subcutaneous physiologic or non-physiologic sensors, patient-input devices and/or information systems.

The pulse generator 505 may optionally incorporate a motion detector 520 that may be used to sense various respiration-related conditions. For example, the motion detector 520 may be optionally configured to sense snoring, activity level, and/or chest wall movements associated with respiratory effort, for example. The motion detector 520 may be implemented as an accelerometer positioned in or on the housing 501 of the pulse generator 505. If the motion sensor is implemented as an accelerometer, the motion sensor may also provide respiratory, e.g. rales, coughing, and cardiac, e.g. S1-S4 heart sounds, murmurs, and other acoustic information.

The lead system 510 of the CRM 500 may incorporate one or more transthoracic impedance sensors that may be used to acquire the patient's respiration waveform, or other respiration-related information. The transthoracic impedance sensor may include, for example, one or more intracardiac electrodes 541, 542, 551-555, 563 positioned in one or more chambers of the heart 590. The intracardiac electrodes 541, 542, 551-555, 563 may be coupled to impedance drive/sense circuitry 530 positioned within the housing of the pulse generator 505.

In one implementation, impedance drive/sense circuitry 530 generates a current that flows through the tissue between an impedance drive electrode 551 and a can electrode on the housing 501 of the pulse generator 505. The voltage at an impedance sense electrode 552 relative to the can electrode changes as the patient's transthoracic impedance changes. The voltage signal developed between the impedance sense electrode 552 and the can electrode is detected by the impedance sense circuitry 530. Other locations and/or combinations of impedance sense and drive electrodes are also possible.

The lead system 510 may include one or more cardiac pace/sense electrodes 551-555 positioned in, on, or about one or more heart chambers for sensing electrical signals from the patient's heart 590 and/or delivering pacing pulses to the heart 590. The intracardiac sense/pace electrodes 551-555, such as those illustrated in FIG. 5A, may be used to sense and/or pace one or more chambers of the heart, including the left ventricle, the right ventricle, the left atrium and/or the right atrium. The lead system 510 may include one or more defibrillation electrodes 541, 542 for delivering defibrillation/cardioversion shocks to the heart.

The pulse generator 505 may include circuitry for detecting cardiac arrhythmias and/or for controlling pacing or defibrillation therapy in the form of electrical stimulation pulses or shocks delivered to the heart through the lead system 510.

Figure 5B:
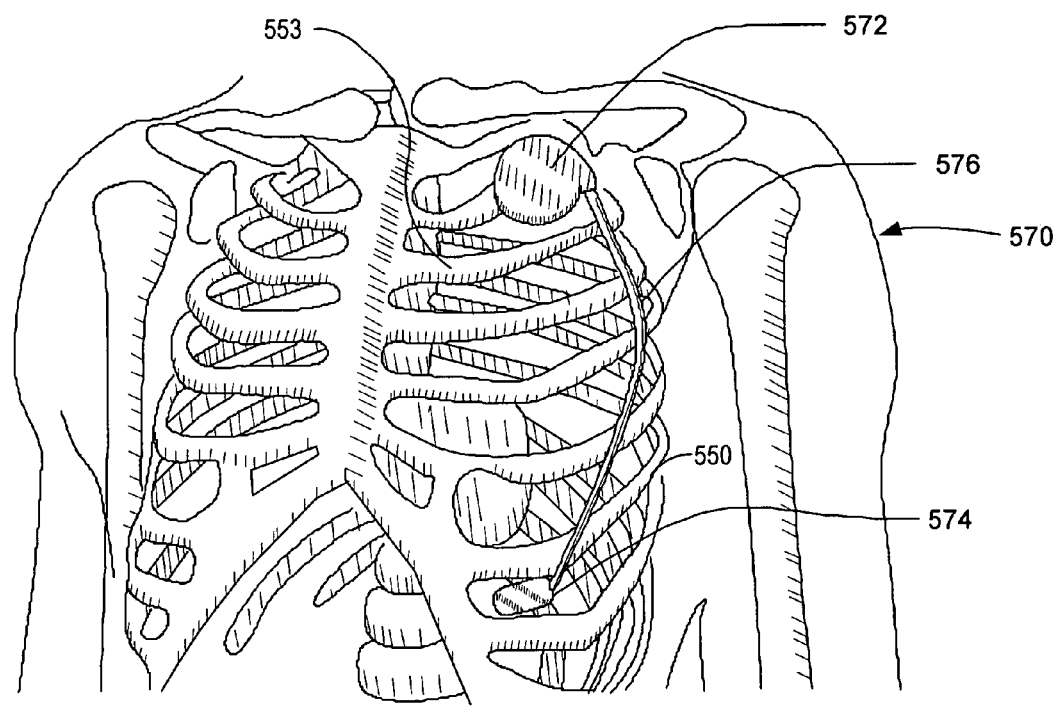
FIG. 5B is a diagram illustrating a subcutaneous implantable medical device that may be used for diagnosis and therapy using patient posture information in accordance with embodiments of the invention.

FIG. 5B is a diagram illustrating a subcutaneous implantable medical device 570 that may include circuitry for implementing portions of the posture detection system in accordance with embodiments of the invention. The device 570 illustrated in FIG. 5B is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of a rib cage 550 at an intercostal or subcostal location, within the abdomen, or in the upper chest region (e.g., subclavian location, such as above a third rib 553). In one implementation, one or more electrodes may be located on a primary housing 572 and/or at other locations about, but not in direct contact with the heart, great vessel or coronary vasculature.

In the particular configuration shown in FIG. 5B, the ITCS device includes the housing 572 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures in general may be implemented in combination with other components and functionality, and that the depiction of such components and functionality in individual or integral form is for purposes of clarity of explanation, and not of limitation.

Communications circuitry may be disposed within the housing 572 for facilitating communication between the ITCS device and an external respiratory therapy device, as well as other devices, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors. The housing 572 is typically configured to include one or more electrodes (e.g., can electrode and/or indifferent electrode). Although the housing 572 is typically configured as an active can, it is appreciated that a non-active can configuration may be implemented, in which case at least two electrodes spaced apart from the housing 572 are employed.

In the configuration shown in FIG. 5B, a subcutaneous electrode 574 may be positioned under the skin in the chest region and situated distal from the housing 572. The subcutaneous and, if applicable, housing electrode(s) may be positioned about the heart at various locations and orientations, such as at various anterior and/or posterior locations relative to the heart. The subcutaneous electrode 574 is coupled to circuitry within the housing 572 via a lead assembly 576. One or more conductors (e.g., coils or cables) are provided within the lead assembly 576 and electrically couple the subcutaneous electrode 574 with circuitry in the housing 572. One or more sense, sense/pace or defibrillation electrodes may be situated on the elongated structure of the electrode support, the housing 572, and/or the distal electrode assembly (shown as subcutaneous electrode 574 in the configuration shown in FIG. 5B).

In one configuration, the electrode support assembly and the housing 572 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the electrode support assembly defines a physically separable unit relative to the housing 572. The electrode support assembly includes mechanical and electrical couplings that facilitate mating engagement with corresponding mechanical and electrical couplings of the housing 572. For example, a header block arrangement may be configured to include both electrical and mechanical couplings that provide for mechanical and electrical connections between the electrode support assembly and housing 572. The header block arrangement may be provided on the housing 572 or the electrode support assembly. Alternatively, a mechanical/electrical coupler may be used to establish mechanical and electrical connections between the electrode support assembly and housing 572. In such a configuration, a variety of different electrode support assemblies of varying shapes, sizes, and electrode configurations may be made available for physically and electrically connecting to a standard ITCS device housing 572.

Various embodiments described herein may be used in connection with subcutaneous monitoring, diagnosis, and/or therapy. Methods, structures, and/or techniques described herein relating to subcutaneous systems and methods may incorporate features of one or more of the following references: commonly owned US Patent Application: Ser. No. 60/462,272 Ser. No. 10/821,248, filed Apr. 8, 2004; and "Subcutaneous Cardiac Rhythm Management," Ser. No. 10/820,642, filed Apr. 8, 2004; now U.S. Publication No. 2004/0215240 and U.S. Pat. No. 7,570,997, each hereby incorporated herein by reference.

Figure 6:
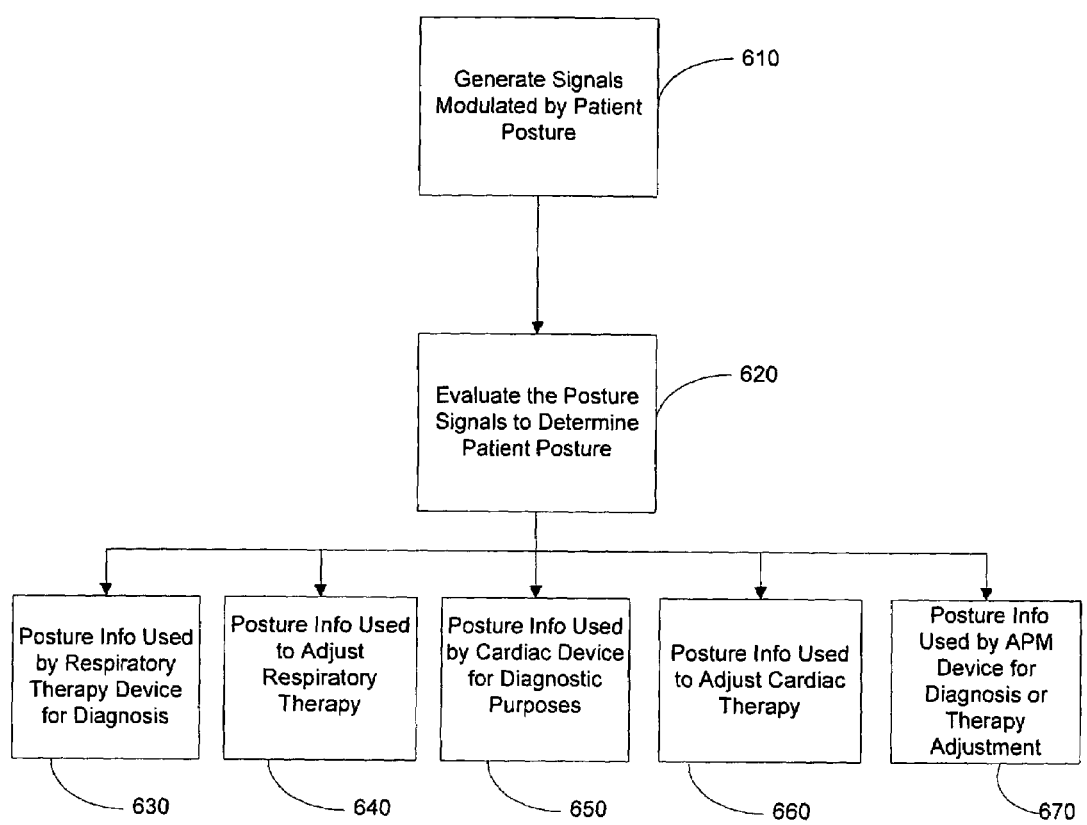
FIG. 6 is a flow chart of uses for posture detection in accordance with the invention.

FIG. 6 is a process flow diagram illustrating various uses for posture information in accordance with the present invention. A posture sensor coupled to a respiratory therapy device generates signals 610 modulated by patient posture. The signals are evaluated 620 to determine various aspects of patient posture. For example, evaluation of the posture sensor signals may provide information about the patient position, such as whether the patient is recumbent or upright, the inclination of the patient's torso, whether the patient is lying on his or her back, left side, right side, or front, and/or other posture or position-related information.

The posture information is transmitted to an implantable device, such as a pacemaker or other implantable cardiac device. The posture information may be used to detect or verify sleep. Additionally or alternatively, the posture information may be used, to diagnose 630 or predict various disorders of the patient, such as disordered breathing, or for other purposes. The implantable CRM device may use the posture information to adjust 640 cardiac electrical stimulation therapy delivered to the patient.

The posture information may also be used by the respiratory therapy device. The respiratory therapy device may use the posture information to detect or verify sleep, to diagnose 650 or predict episodes of disordered breathing. The posture information may be used respiratory therapy device to modify 660 the therapy delivered by the respiratory therapy device.

The implantable device, respiratory therapy device, or both may be coupled to an APM system. Posture information may be relayed to the APM system. The APM system may store the posture information, use 670 the posture information to monitor the patient, diagnose various disorders affecting the patient, and/or to adjust patient therapy. The APM system may transmit the posture information to a variety of other devices connected through the APM system.

A number of the examples presented herein involve block diagrams illustrating functional blocks used for in accordance with embodiments of the present invention. It will be understood by those skilled in the art that there exist many possible configurations in which these functional blocks can be arranged and implemented.

The examples depicted herein provide examples of possible functional arrangements used to implement the approaches of the invention. The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

Methods, devices, and systems in accordance with the present invention may incorporate one or more of the features, structures, methods, or combinations thereof described herein. For example, a medical system may be implemented to include one or more of the features and/or processes described herein. It is intended that such a method, device, or system need not include all of the features and functions described herein, but may be implemented to include one or more selected features and functions that provide unique structures and/or functionality.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A posture detection system, comprising:
   an implantable cardiac device;
   a patient-external respiratory therapy device comprising a posture sensor configured to be coupled to the patient;
   a processor and memory, the processor configured to execute instructions stored in the memory; and
   a communications channel between the implantable cardiac device and the patient-external respiratory therapy device, the communications channel configured to transfer posture information between the implantable cardiac device and the patient-external therapy respiratory device, wherein processor execution of the stored instructions causes one or both of the implantable cardiac device and the patient-external respiratory therapy device to detect episodes of sleep disordered breathing, correlate detected episodes of sleep disordered breathing to postural positions based on the posture information, provide an output based on the correlation, and enhance subsequent detection of disordered breathing episodes using correlation relationships between postural positions and episodes of disordered breathing.

2. The system of claim 1, wherein the posture detector is configured to determine a positional orientation of the patient's head.

3. The system of claim 1, wherein the posture detector is configured to determine a positional orientation of a portion of a patient's body.

4. The system of claim 1, wherein processor execution of the stored instructions causes one or both of the implantable cardiac device and the patient-external respiratory therapy device to use correlation relationships between postural positions and episodes of disordered breathing to predict subsequent episodes of disordered breathing.

5. The system of claim 1, wherein processor execution of the stored instructions causes one or both of the implantable cardiac device and the patient-external respiratory therapy device to predict episodes of disordered breathing based on posture.

6. The system of claim 1, wherein correlating detected episodes of sleep disordered breathing to postural positions further comprises correlating particular patient positions to episodes of disordered breathing.

7. The system of claim 1, wherein the posture detector comprises an accelerometer configured to output a waveform signal and wherein changes in the waveform signal correspond to postural changes of the patient.

8. The system of claim 1, wherein the posture detector comprises an inclination sensitive sensor.

9. The system of claim 1, wherein the implantable device comprises a cardiac therapy device.

10. The system of claim 9, wherein processor execution of the stored instructions causes the cardiac therapy device to modify cardiac electrical stimulation therapy based on the patient posture information, the modification comprising switching between a uni-ventricular pacing mode to a bi-ventricular pacing mode.

11. The system of claim 1, wherein processor execution of the stored instructions causes the implantable device to modify a cardiac electrical stimulation therapy treating disordered breathing based on the patient posture information.

12. The system of claim 1, wherein processor execution of the stored instructions causes the external respiratory therapy device to modify external respiratory therapy based on the patient posture.

13. A posture detection method, comprising:
    detecting episodes of sleep disordered breathing;
    detecting postural positions of a patient using a sensor of a patient-external respiratory therapy device;
    correlating detected postural positions to the detected episodes of sleep disordered breathing;
    transmitting posture information between the patient-external respiratory therapy device and the implantable cardiac device; and
    adjusting disordered breathing therapy based on the posture information, wherein detecting episodes of sleep disordered breathing further comprises using one or more correlation relationships between the detected postural positions and the detected episodes of disordered breathing to enhance subsequent detection of disordered breathing episodes.

14. The method of claim 13, wherein adjusting the disordered breathing therapy comprises adjusting an externally delivered disordered breathing therapy.

15. The method of claim 13, further comprising adjusting a cardiac therapy delivered by the implantable cardiac device based on the posture information, the cardiac therapy comprising a cardiac electrical stimulation therapy treating disordered breathing.

16. The method of claim 13, wherein correlating detected episodes of sleep disordered breathing to postural positions comprises correlating particular patient positions to episodes of disordered breathing.

17. The method of claim 13, further comprising predicting subsequent episodes of disordered breathing based on one or more correlation relationships between the detected postural positions and the detected episodes of sleep disordered breathing.

18. A posture detection system, comprising:
    means for detecting episodes of sleep disordered breathing;
    means for detecting postural positions using a sensor of one of a patient-external respiratory therapy device and an implantable cardiac device;
    means for correlating detected postural positions to the detected episodes of sleep disordered breathing;
    means for transmitting posture information between the patient-external respiratory therapy device and the implantable cardiac device;
    means for predicting subsequent episodes of disordered breathing based on correlation between the detected postural positions and the detected episodes of sleep disordered breathing; and
    means for adjusting disordered breathing therapy based on the detected patient posture.

19. The system of claim 18, wherein means for adjusting disordered breathing therapy comprises means for adjusting a cardiac therapy treating disordered breathing based on the detected patient posture.

20. The system of claim 18, wherein means for adjusting disordered breathing therapy comprises means for adjusting a patient-external respiratory therapy based on the detected patient posture.

21. The system of claim 18, further comprising means for using correlation relationships between the detected postural positions and the detected episodes of disordered breathing to enhance subsequent detection of disordered breathing episodes.

* * * * *

UNITED STATES PATENT AND TRADEMARK OFFICE
CERTIFICATE OF CORRECTION

PATENT NO. : 7,664,546 B2 Page 1 of 1
APPLICATION NO. : 10/943079
DATED : February 16, 2010
INVENTOR(S) : Hartley et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 548 days.

Signed and Sealed this

Twenty-eighth Day of December, 2010

David J. Kappos
*Director of the United States Patent and Trademark Office*